US008716556B2

(12) United States Patent
Park et al.

(10) Patent No.: US 8,716,556 B2
(45) Date of Patent: May 6, 2014

(54) USE OF MYB96 GENE FROM *ARABIDOPSIS THALIANA* TO INCREASE CUTICULAR WAX BIOSYNTHESIS

(75) Inventors: Chung Mo Park, Gyeonggi-do (KR); Pil Joon Seo, Jeollabuk-do (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 13/990,459

(22) PCT Filed: Jan. 4, 2011

(86) PCT No.: PCT/KR2011/000018
§ 371 (c)(1),
(2), (4) Date: May 30, 2013

(87) PCT Pub. No.: WO2012/074165
PCT Pub. Date: Jun. 7, 2012

(65) Prior Publication Data
US 2013/0254936 A1 Sep. 26, 2013

(30) Foreign Application Priority Data
Dec. 3, 2010 (KR) .................. 10-2010-0122853

(51) Int. Cl.
C12N 15/29 (2006.01)
C12N 15/05 (2006.01)
C12P 7/64 (2006.01)
C12P 7/06 (2006.01)
A01H 1/00 (2006.01)
C12N 15/82 (2006.01)

(52) U.S. Cl.
USPC ........... 800/281; 800/306; 435/134; 435/161; 536/23.6

(58) Field of Classification Search
None
See application file for complete search history.

(56) References Cited

U.S. PATENT DOCUMENTS 4,940,838 A 7/1990 Schilperoort

FOREIGN PATENT DOCUMENTS

| EP | 0116718 A1 | 8/1984 | |
|---|---|---|---|
| EP | 0301316 A2 | 2/1989 | |
| EP | 0120516 B1 | 10/1991 | |
| EP | 1586645 A2 * | 10/2005 | ............. C12N 15/29 |
| KR | 10-2007-0110615 A | 11/2007 | |
| KR | 10-2009-0095631 A | 9/2009 | |
| KR | 10-2010-0031527 A | 3/2010 | |

OTHER PUBLICATIONS

Zhang et al 2005 The Plant Journal 42: p. 689-707.*
International Search Report for PCT/KR2011/000018.

Pil Joon Seo et al. "The MYB96 Transcription Factor Mediates Abscisic Acid Signaling during Drought Stress Response in *Arabidopsis*", Plant Physiology, Sep. 2009, vol. 151, pp. 275-289 See "MYB96 Is Induced by ABA and Drought" of pp. 276-278, "Subcellular Localization of MYB96 and Histological Assays" and figure 2 of p. 287.
Marie Javell et al. "Overexpression of the Epidermis-Specific Homeodomain-Leucine Zipper IV Transcription Factor Outer Cell La Yeri in Maize Identifies Target Genes Involved in Lipid Metabolism and Cuticle Biosynthesis", Plant Physiology, Sep. 2010, vol. 154, pp. 273-286—See abstract of p. 273, "Regulation of Cuticle Biosynthesis" of p. 283.
Ji-Yi Zhang et al. "Overexpression of WXP 1, a putative Medicago truncatula AP2 domain-containing transcription factor gene, increases in circular wax accumulation and enhances drought tolerance in transgenic alfalfa (*Medicago sativa*)", the Plant Journal, 2005, vol. 42, pp. 689-707—See the entire document.
Ji-Yi Zhang et al., "Heterologous expression of two Medicago truncatula putative ERF transcription Factor genes, Wxpi and WXP2, in *Arabidopsis* led to increased leaf wax accumulation and improved drought tolerance, but differential response in freezing tolerance"—See the entire document.
Crossway A. et al., 1986, Mol. Gen. Genet. 202, 179-185.
Klein T.M. et al., 1987, Nature 327, 70.
Hanahan, D., J. Mol. Biol., 166:557-580(1983).
Zuo et al., Plant J. 24, 265-273,2000.
Wu et al., J. Am. Stat. Assoc. 99,909-917, 2004.
Gentleman, et al., Genome Biol. 5, R80, 2004.
Lee et al, Plant J. 60, 462-475,2009.
Pighin et al, Science 306, 702-704, 2004.
Lawrence et al.,Mol. Cell 13, 599-609, 2004.
Miura et al., Plant Cell 19, 1403-1414, 2007.
Lolle et al., Genetics 149,607-619, 1998.
Sirichandra et al., J. Exp. Bot. 60, 1439-1463, 2009.
Negrutiu I. et al., Jun. 1987, Plant Mol. Biol. 8, 363-373.
Beaudoin et al., Plant Physiol. 150, 1174-1191, 2009.
Suh et al., Plant Physiol. 139, 1649-1665, 2005.
Schnurr et al., Plant Cell 16,629-642, 2004.
Chen et al.,Plant Cell 15, 1170-1185, 2003.
Aharoni et al., Plant Cell 16,2463-2480, 2004.
Raffaele et al., Plant Cell 20, 752-767, 2008.
Abe et al., Plant Cell 15, 63-78,2003.

(Continued)

*Primary Examiner* — David T Fox
*Assistant Examiner* — Matthew Keogh
(74) *Attorney, Agent, or Firm* — The PL Law Group, PLLC

(57) ABSTRACT

A method for increasing cuticular wax biosynthesis of plant includes transforming a plant cell with the recombinant vector containing MYB96 (myb domain protein 96) gene from *Arabidopsis thaliana*. A method for producing a transgenic plant with increased cuticular wax biosynthesis includes transforming a plant cell with the recombinant vector containing the MYB96 gene, and regenerating the transformed plant cell into the transgenic plant. A plant and a seed with increased cuticular wax biosynthesis are produced by the method. A method for producing a biofuel using a cuticular wax includes separating and purifying a cuticular wax from the plant. A composition for increasing cuticular wax biosynthesis of plant includes the MYB96 gene.

6 Claims, 13 Drawing Sheets

(56) References Cited

OTHER PUBLICATIONS

Kunst and Samuels, Curr. Opin. Plant Biol. 12, 721-727, 2009.
Cominelli et al., Plant J. 53,53-64, 2008.
Schirmer et al., Science 329, 559-562,2010.
Krens, F.A. et al., 1982, Nature 296, 72-74.
Shillito R.D. et al., 1985 Bio/Technol. 3, 1099-1102.

\* cited by examiner

FIG. 1A

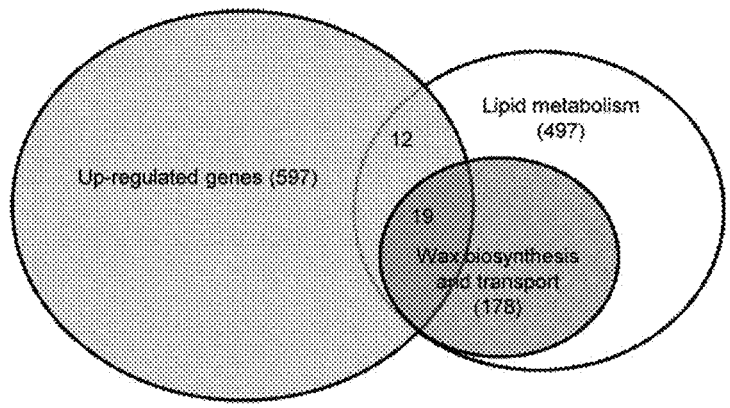

FIG. 1B

| Wax biosynthesis | | | | |
|---|---|---|---|---|
| Group | AGI | FC | Gene symbol | Annotation |
| VII | AT1G57750 | 50.60 | MAH1 | Midchain alkane hydroxylase/CYP96A15 |
| XI | AT5G55450 | 15.06 | LTP | Lipid transfer protein type 3 |
| XI | AT5G59320 | 12.49 | LTP3 | Nonspecific lipid-transfer protein |
| IX | AT5G37300 | 11.30 | WSD1 | Bifunctional wax ester synthase |
| VIII | AT4G33790 | 7.42 | CER4/FAR3 | Alcohol-forming fatty acyl-CoA reductase |
| III | AT1G04220 | 6.57 | KCS2/DAISY | Ketoacyl-CoA synthase |
| VI | AT5G57800 | 4.61 | CER3/WAX2/YRE/FLP1 | Unknown |
| III | AT1G68530 | 4.10 | KCS6/CER6/CUT1 | Ketoacyl-CoA synthase |
| V | AT3G55360 | 3.24 | ECR/CER10/ATTSC13 | Enoyl-CoA-reductase |
| X | AT1G17840 | 3.07 | WBC11/ABCG11/COF1 | ABC transporter |
| II | AT1G36160 | 3.04 | ACC1 | Acetyl-CoA carboxylase |
| I | AT1G64400 | 3.00 | LACS3 | Long-chain acyl-CoA synthetase |
| III | AT2G28630 | 2.91 | KCS12 | Ketoacyl-CoA synthase |
| IV | AT1G67730 | 2.89 | KCR1 | Ketoacyl-CoA reductase |
| III | AT1G01120 | 2.65 | KCS1 | Ketoacyl-CoA synthase |
| XI | AT2G38530 | 2.56 | LTP2 | Nonspecific lipid-transfer protein |
| VI | AT1G02205 | 2.23 | CER1 | Unknown |
| X | AT3G21090 | 2.22 | WBC15/22/ABCG15 | ABC transporter |
| X | AT3G55130 | 2.06 | WBC19/ABCG19 | ABC transporter |

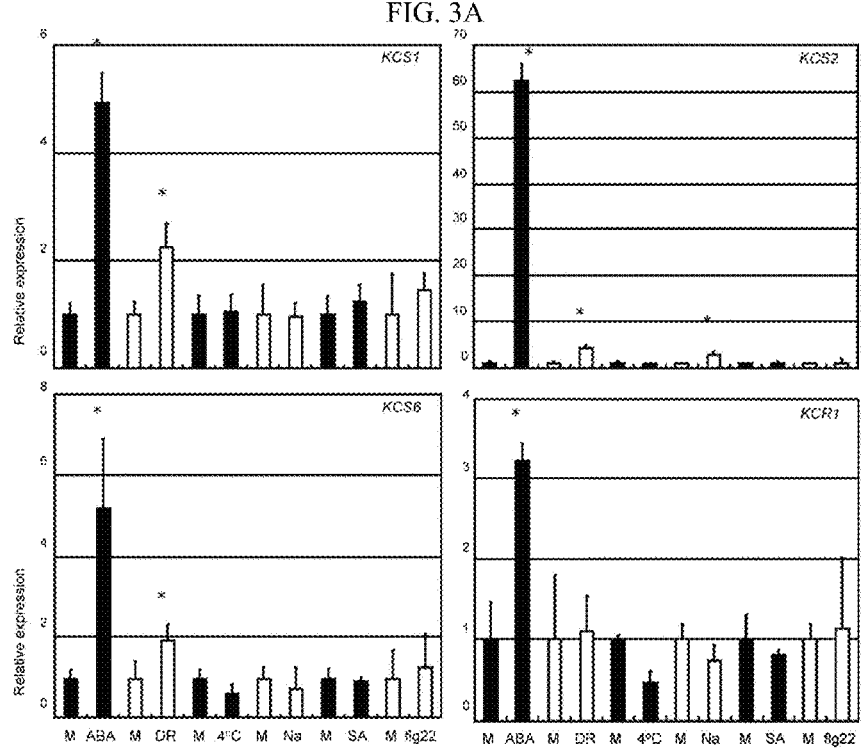

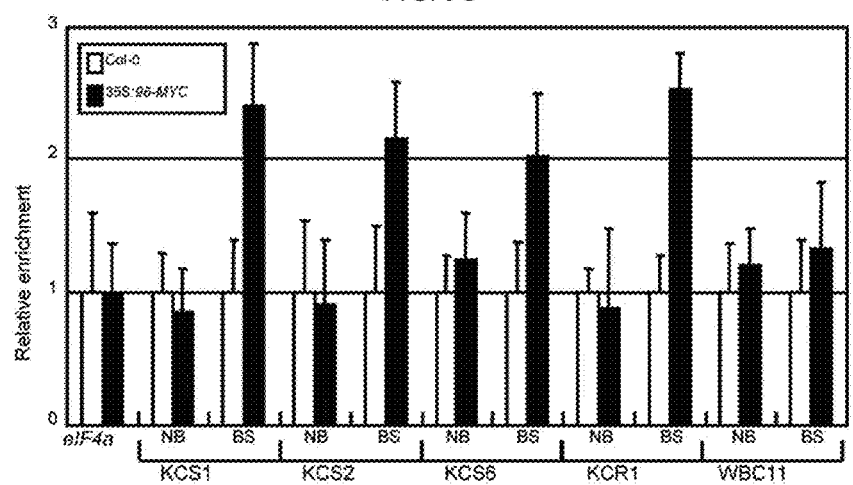

USE OF MYB96 GENE FROM *ARABIDOPSIS THALIANA* TO INCREASE CUTICULAR WAX BIOSYNTHESIS

CROSS REFERENCE TO RELATED APPLICATIONS AND CLAIM OF PRIORITY

This patent application is a National Phase application under 35 U.S.C. §371 of International Application No. PCT/KR2011/000018, filed Jan. 4, 2011, which claims priority to Korean Patent Application No. 10-2010-0122853 filed Dec. 3, 2010, entire contents of which are incorporated herein by reference.

BACKGROUND

1. Technical Field

The present invention relates to a MYB96 gene from *Arabidopsis thaliana* and its use. More specifically, the present invention relates to a method for increasing cuticular wax biosynthesis of plant by transforming a plant cell with the recombinant vector containing MYB96 (myb domain protein 96) gene from *Arabidopsis thaliana*, a method for producing a transgenic plant with increased cuticular wax biosynthesis with the recombinant vector containing the MYB96 gene, a plant and a seed with increased cuticular wax biosynthesis produced by the method, a method for producing a biofuel using a cuticular wax comprising separating and purifying a cuticular wax from the plant, and a composition for increasing cuticular wax biosynthesis of plant comprising the MYB96 gene.

2. Description of the Related Art

Fossil fuel widely used as various fuels and industrial raw materials are limited and emit a significant amount of greenhouse gas responsible for global warming, thus research and development of energy that can replace it is urgent. Accordingly, all over the world spurred the development of biofuels which can replace fossil fuels and cause less environmental pollution, in particular the development of biofuels using corn and sugarcane, and the like is attracting attention. However, the production of biofuels using food resources such as corn can cause problems such as the lack of food resources and the rise in grain prices. In addition, since it requires a large area of arable land in order to produce biofuel smoothly, secondary destruction of the ecosystem such as clearing forests in order to secure the raw materials can be made.

Biofuel means sustainable energy sources made from biomass in the nature. Biomass is a concept that encompasses the organic matter of organisms such as animals, plants, and microorganisms, and its kind such as various by-products and waste products derived from agriculture and forestry comprising various plants and animals, food waste, industrial waste based on the organisms, and crops (energy crops, etc.) grown for biofuel production is very diverse. The biomass can be converted into solid, liquid, and gaseous biofuels by the application of physical, chemical, and biological technologies. As a kind of biofuels, bioalcohol (such as bioethanol and biomethanol), and biodiesel is representative. Bioalcohol and biodiesel are used as a fuel alternative to gasoline and diesel, respectively.

According to Korean Patent Publication No. 2010-0031527, a method for producing a biofuel using a microorganism is described. Furthermore, according to Korean Patent Publication No. 2009-0095631, a method for producing a biofuel from lipid biomass is described.

SUMMARY

The present invention is devised in view of the above-described needs. The inventors of the present invention confirmed that MYB96 transcription factor directly regulates cuticular wax biosynthetic genes under drought, thereby inducing cuticular wax biosynthesis and accumulation and therefore completed the invention.

In order to solve the problems described above, the present invention provides a method for increasing cuticular wax biosynthesis of plant by transforming a plant cell with the recombinant vector containing MYB96 (myb domain protein 96) gene from *Arabidopsis thaliana*.

Further, the present invention provides a method for producing a transgenic plant with increased cuticular wax biosynthesis with the recombinant vector containing the MYB96 gene.

Further, the present invention provides a plant and a seed with increased cuticular wax biosynthesis produced by the method.

Further, the present invention provides a method for producing a biofuel using a cuticular wax comprising separating and purifying a cuticular wax from the plant.

Further, the present invention provides a composition for increasing cuticular wax biosynthesis of plant comprising the MYB96 gene.

According to the present invention, a cuticular wax biosynthesis and accumulation was increased in the plant transformed with MYB96 gene from *Arabidopsis thaliana* and the content of fatty acid, alcohol and alkane in the composition of the cuticular wax was increased. Therefore, if using the increased cuticular wax, it can be useful to develop a biofuel.

BRIEF DESCRIPTION OF THE DRAWINGS

FIGS. 1A to 1D shows that wax biosynthetic genes are up-regulated in myb96-1D. FIG. 1A shows Venn diagrams showing the distribution of overlapping and nonoverlapping genes encoding lipid metabolic and wax biosynthetic enzymes. FIG. 1B shows a list of wax biosynthetic genes up-regulated in myb96-1D. FC, fold change. FIG. 1C shows the simplified wax biosynthetic pathway. FIG. 1D shows qRT-PCR of wax biosynthetic gene expression.

FIG. 2A shows SEM images, and FIGS. 2B and 2C are graphs showing the cuticular wax composition and loads on the leaves.

FIGS. 3A and 3B show that drought induction of cuticular wax biosynthetic genes requires MYB96.

FIG. 4A shows accumulation of cuticular waxes under drought. FIG. 4B shows the cuticular wax composition in the leaves under drought. FIG. 4C shows the induction of wax biosynthetic genes. FIG. 4D shows the elevation of cuticular wax crystals after β-estradiol induction of MYB96.

FIGS. 5A through 5F show that MYB96 binds to consensus motifs in the wax biosynthetic gene promoters. FIG. 5A shows MYB-binding consensus sequences (BSs) (SEQ ID NO: 4). FIG. 5B shows in vitro binding of MYB96 to the consensus sequences. FIG. 5C shows the results of ChIP assays. 35S:96-MYC transgenic plants grown on MS-agar plates for 3 weeks were used. FIG. 5D shows the expression constructs used. Min 35S, a minimal CaMV 35S promoter; Nos-T, Nos terminator. FIG. 5E shows the results of the transcriptional activation activity assays in *Arabidopsis* protoplasts. FIG. 5F shows the schematic working model of MYB96 function in cuticular wax biosynthesis under drought.

DETAILED DESCRIPTION

Exemplary embodiments of the present invention will be described in detail below with reference to the accompanying drawings.

Figure 1C:
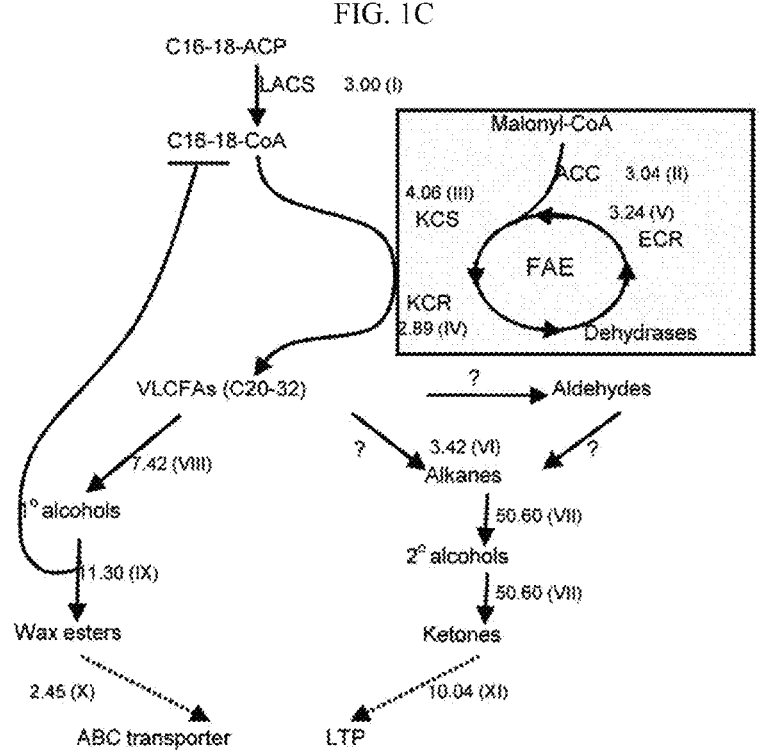
Figure 1D:
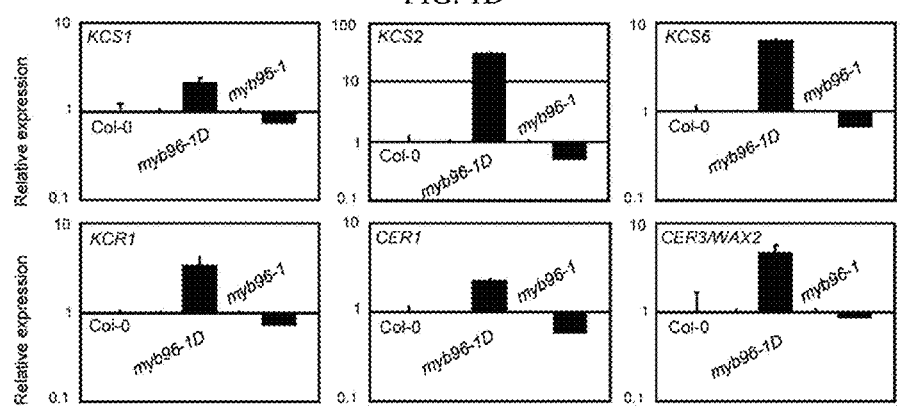

FIGS. 1A to 1D shows that wax biosynthetic genes are up-regulated in myb96-1D. FIG. 1A shows Venn diagrams showing the distribution of overlapping and nonoverlapping genes encoding lipid metabolic and wax biosynthetic enzymes. FIG. 1B shows a list of wax biosynthetic genes up-regulated in myb96-1D. FC, fold change. FIG. 1C shows the simplified wax biosynthetic pathway (Kunst and Samuels, *Curr. Opin. Plant Biol.* 12, 721-727, 2009). Numbers indicate mean fold change of the genes belonging to individual gene groups (I to XI), as marked in FIG. 1B. FIG. 1D shows qRT-PCR of wax biosynthetic gene expression. Two-week-old whole plants grown on MS-agar plants were used to extract total RNAs. Biological triplicates were averaged. Bars indicate standard error of the mean. The vertical axis is displayed on a logarithmic scale.

Figure 2A:
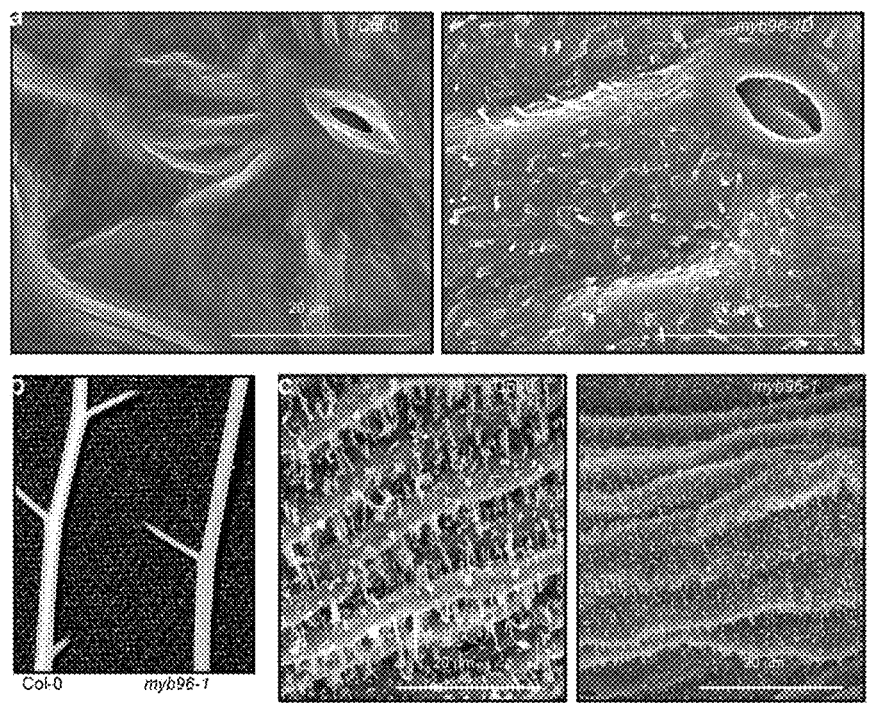
FIG. 2A through C show that cuticular wax deposition is altered in myb96-1D and myb96-1 mutants.
Figure 2B:
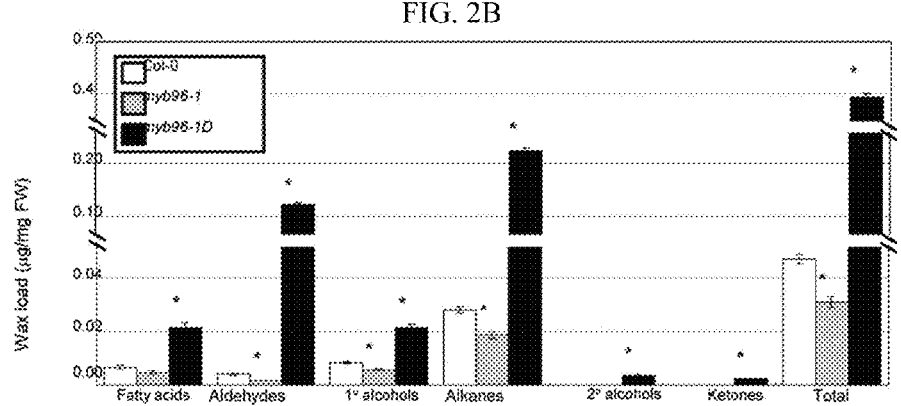
Figure 2C:
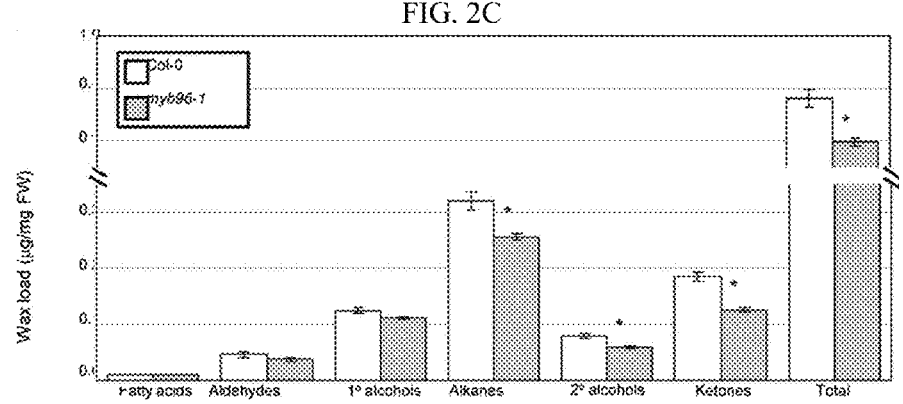

FIG. 2A through C show that cuticular wax deposition is altered in myb96-1D and myb96-1 mutants. FIG. 2A shows (a) SEM images of cuticular wax crystals on the leaves, (b) Waxless appearance of the myb96-1 stem, and (c) SEM images of cuticular wax crystals on the stems. FIGS. 2B and 2C are graphs showing the cuticular wax composition and loads on the leaves (FIG. 2B) and stems (FIG. 2C). Six measurements were averaged and statistically treated using Student t-test. Bars indicate standard error of the mean (*P<0.01).

Figure 3B:
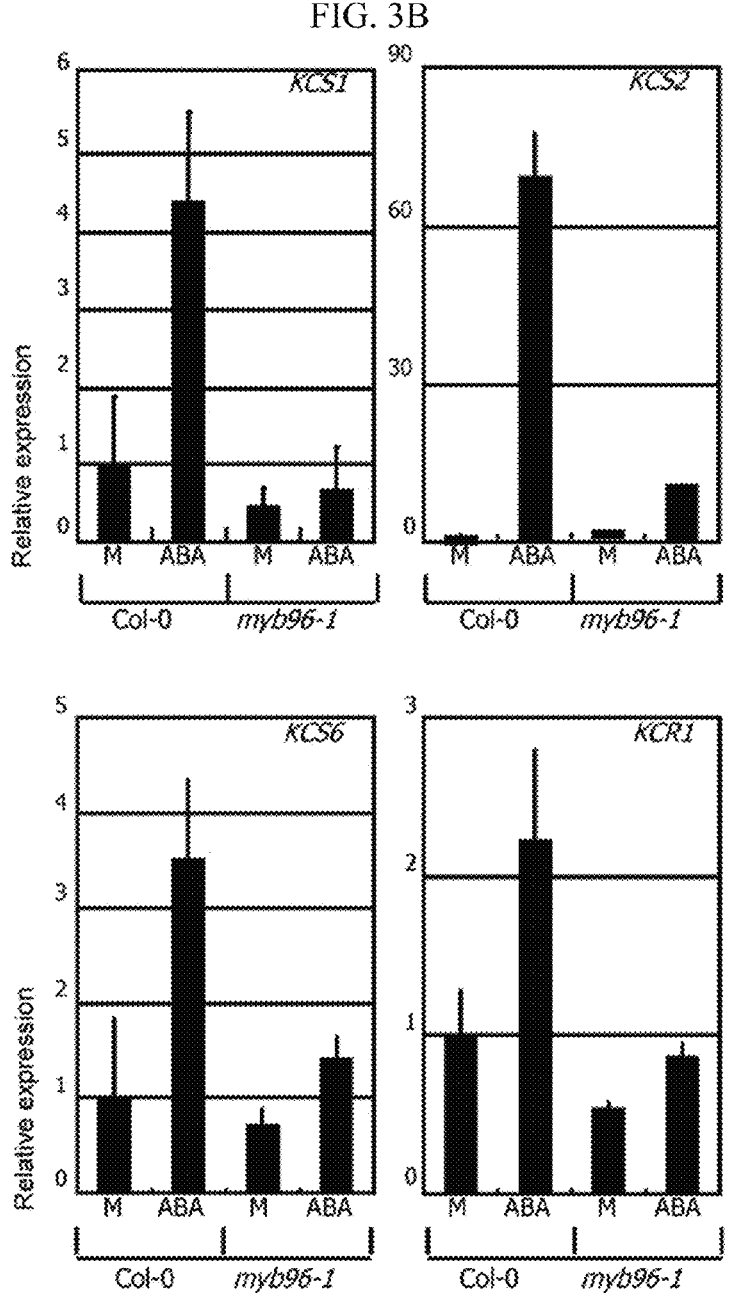

FIGS. 3A and 3B show that drought induction of cuticular wax biosynthetic genes requires MYB96. In FIGS. 3A and 3B, two-week-old plants grown on MS-agar plates were treated with growth hormones, such as 20 μM ABA (6 h) and 100 μM SA (6 h), and stress conditions, including drought (DR, 2 h), cold (4° C., 24 h), 150 mM NaCl (Na, 6 h), and 5 μM flagellin22 (flg22, 24 h), before harvesting whole plant materials. Transcript levels were examined as described in FIG. 1D. Bars indicate standard error of the mean (t-test, *P<0.01). FIG. 3A shows effects of growth hormones and stresses on gene expression. FIG. 3B shows effects of ABA on gene expression in myb96-1.

Figure 4A:
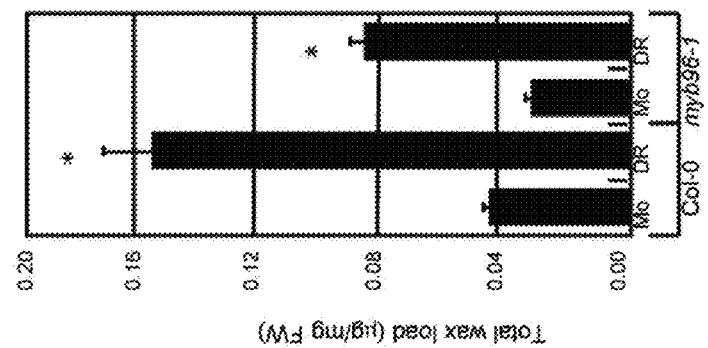
FIGS. 4A through 4D show that cuticular waxes accumulate under drought.
Figure 4B:
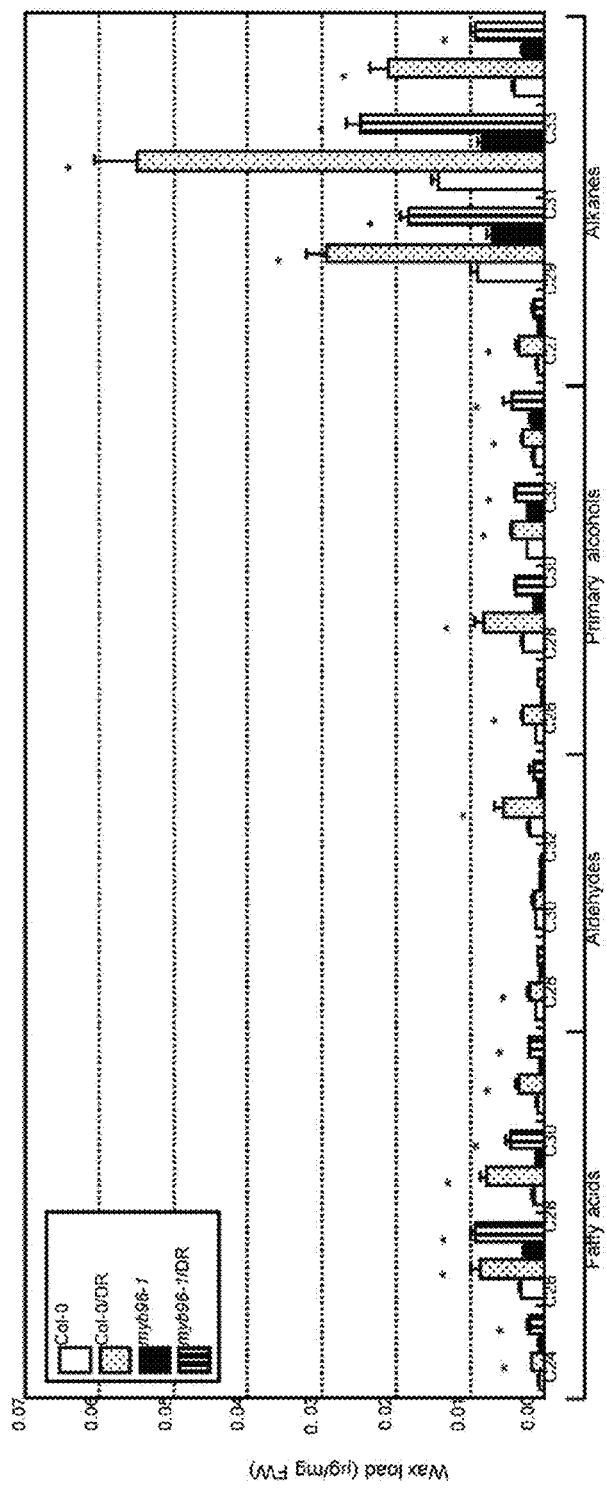
Figure 4C:
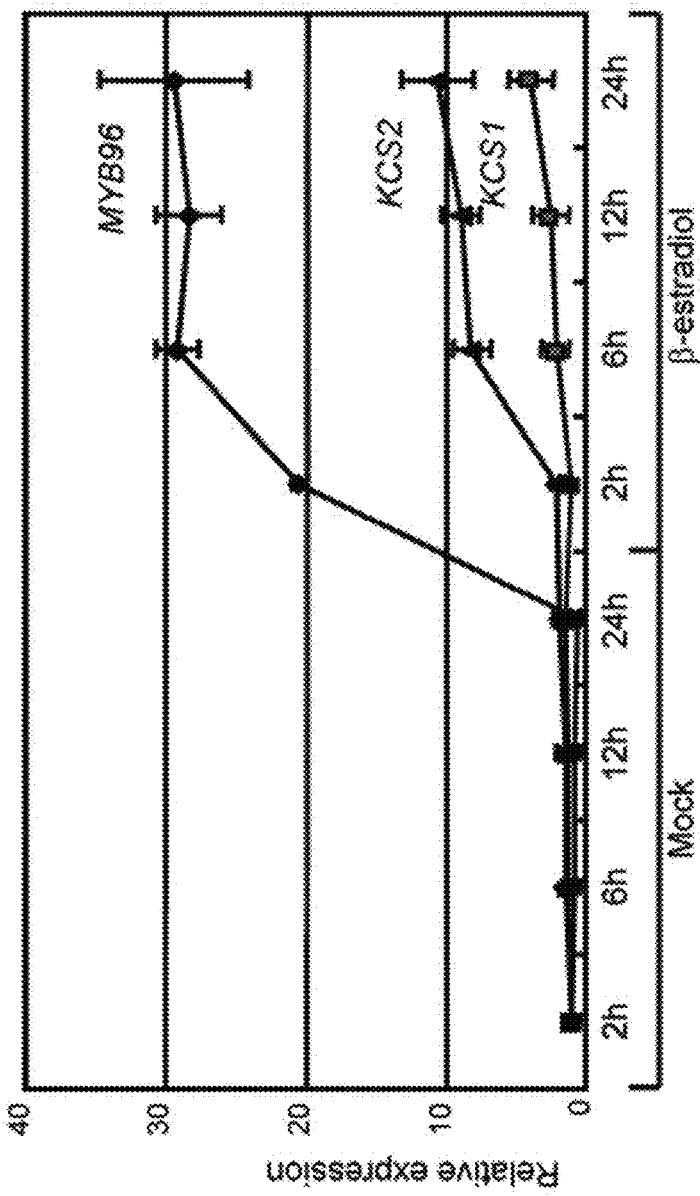
Figure 4D:
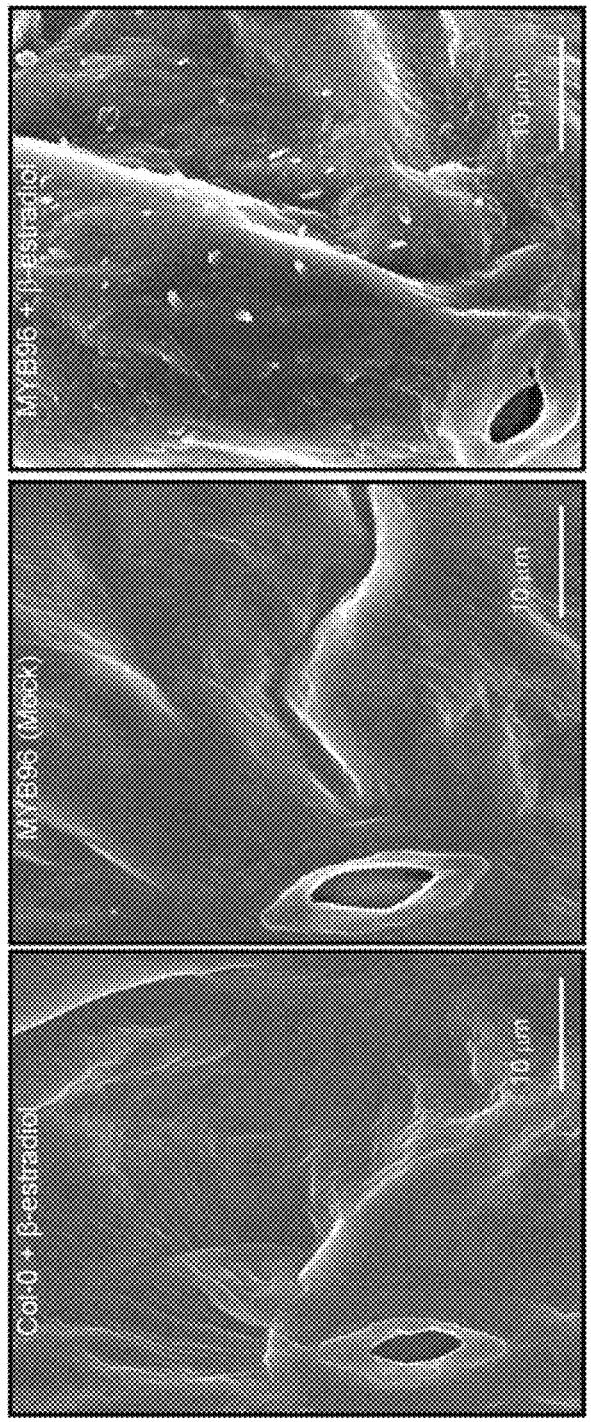

FIGS. 4A through 4D show that cuticular waxes accumulate under drought. FIG. 4A shows accumulation of cuticular waxes under drought. Six measurements were averaged and statistically treated. Bars indicate standard error of the mean (t-test, *P<0.01). FIG. 4B shows the cuticular wax composition in the leaves under drought. Three-week-old leaves were used. Six measurements were averaged and statistically treated. Bars indicate standard error of the mean (t-test, *P<0.01). FIG. 4C shows the induction of wax biosynthetic genes and FIG. 4D shows the elevation of cuticular wax crystals after β-estradiol induction of MYB96. One-week-old plants grown in soil were sprayed every 3 days with 10 μM β-estradiol solution. Cuticular wax crystals were examined by SEM 3 weeks after induction.

Figures 5A, 5B:
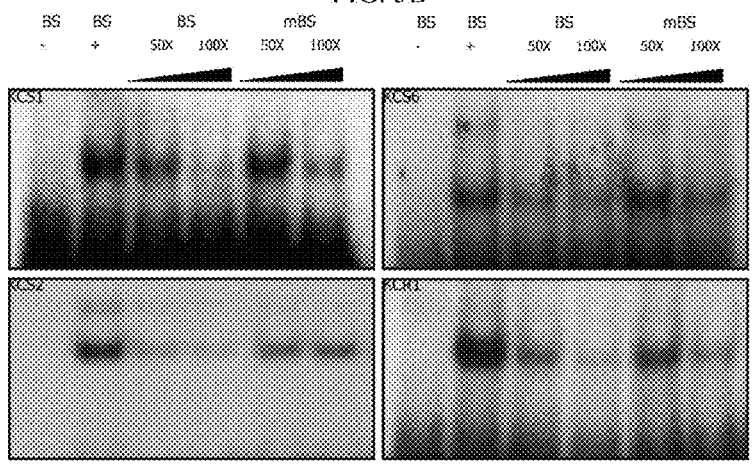
Figure 5E:
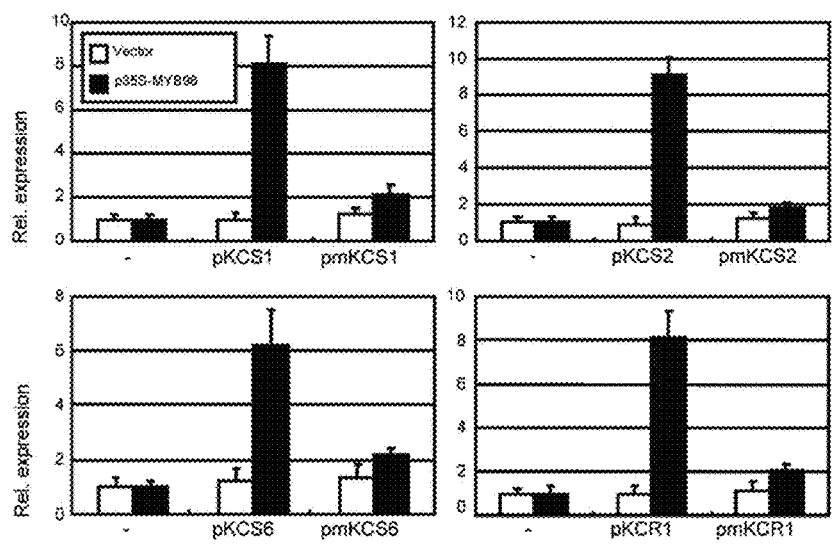
Figure 5F:
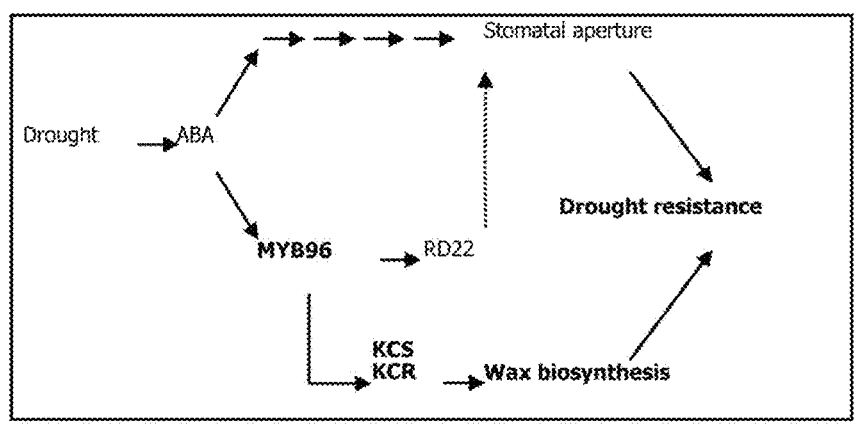

FIGS. 5A through 5F show that MYB96 binds to consensus motifs in the wax biosynthetic gene promoters. FIG. 5A shows MYB-binding consensus sequences (BSs) (SEQ ID NO: 4). Core binding sequences, marked by bold, were mutated, resulting in mBSs (SEQ ID NO: 5), to verify specific binding. FIG. 5B shows in vitro binding of MYB96 to the consensus sequences. The (−) lanes are controls without recombinant MBP-MYB96 proteins. Excess amounts of unlabeled DNA fragments were added as competitors. FIG. 5C shows the results of ChIP assays. 35S:96-MYC transgenic plants grown on MS-agar plates for 3 weeks were used. Three measurements were averaged for individual assays. Bars indicate standard error of the mean (t-test, P<0.01). FIG. 5D shows the expression constructs used. MM 35S, a minimal CaMV 35S promoter; Nos-T, Nos terminator. FIG. 5E shows the results of the transcriptional activation activity assays in *Arabidopsis* protoplasts. Three measurements were averaged. Bars indicate standard error of the mean. FIG. 5F shows the schematic working model of MYB96 function in cuticular wax biosynthesis under drought.

In order to achieve the purpose of the invention described as above, the present invention provides a method for increasing cuticular wax biosynthesis of plant, comprising transforming a plant cell with the recombinant vector containing MYB96 (myb domain protein 96) gene from *Arabidopsis thaliana* to overexpress the MYB96 gene.

Preferably, the MYB96 gene of the present invention may comprise the nucleotide sequence represented by SEQ ID NO: 1. Further, variants of said nucleotide sequence are also within the scope of the present invention. The variants are nucleotide sequences with its nucleotide sequence changed, but having similar functional characteristics with nucleotide sequence represented by SEQ ID NO: 1. Specifically, said gene may comprise a nucleotide sequence with at least 70%, preferably at least 80%, more preferably at least 90%, and still more preferably at least 95% identity with the nucleotide sequences of SEQ ID NO: 1. The "sequence identity %" for a certain polynucleotide is determined by comparing two nucleotide sequences that are optimally arranged with a region to be compared. In this regard, a part of the polynucleotide sequence in a region to be compared may comprise an addition or a deletion (i.e., a gap) compared to a reference sequence (without any addition or deletion) relative to the optimized arrangement of the two sequences.

Preferably, the cuticular wax may have increased content of fatty acid, alcohol or alkane, but not limited thereto.

The term "recombinant" indicates a cell which replicates a heterogeneous nucleotide or expresses said nucleotide, a peptide, a heterogeneous peptide, or a protein encoded by a heterogeneous nucleotide. Recombinant cell can express a gene or a gene fragment in a form of a sense or antisense, which are not found in natural state of cell. In addition, a recombinant cell can express a gene that is found in the natural state, provided that said gene is modified and re-introduced into the cell by an artificial means.

In the present invention, the MYB96 DNA sequence can be inserted into a recombinant expression vector. The term "recombinant expression vector" means bacterial plasmid, phage, yeast plasmid, plant cell virus, mammalian cell virus, or other vectors. Altogether, any plasmid and vector can be used provided that they are capable of replicating and stabilizing in the host. An important feature of the expression vector is having a replication origin, a promoter, a maker gene, and a translation control element.

An expression vector containing MYB96 DNA sequence and appropriate transcription/translation control signals can be constructed using methods well known to those skilled in the art. These methods include in vitro recombinant DNA techniques, DNA synthesis techniques, in vivo recombinant techniques, and the like. Said DNA sequence can be effectively linked to an appropriate promoter in the expression vector in order to direct mRNA synthesis. An expression vector may also comprise a ribosome binding site as a translation initiation site and a transcription terminator.

A preferred example of the recombinant vector is Ti-plasmid vector which can transfer a part of itself, i.e., so-called T-region, to a plant cell when the vector is present in an appropriate host such as *Agrobacterium tumefaciens*. Other types of Ti-plasmid vector (see, EP 0 116 718 B1) are currently used for transferring a hybrid gene to protoplasts that can produce a new plant by appropriately inserting a plant cell or hybrid DNA to a plant genome. Especially preferred form of Ti-plasmid vector is a so-called binary vector which has been disclosed in EP 0 120 516 B1 and U.S. Pat. No. 4,940,838. Other appropriate vectors that can be used for introducing the DNA of the present invention to a host plant can be selected from a double-stranded plant virus (e.g., CaMV), a single-stranded plant virus, and a viral vector which can be originated from Gemini virus, etc., for example a non-complete plant viral vector. Use of said vector can be especially advantageous when a plant host cannot be appropriately transformed.

Expression vector preferably comprises at least one selection marker. Said selection marker is a nucleotide sequence having a property which allows a selection based on a common chemical method. Any kind of gene that can be used for the differentiation of transformed cells from non-transformed cells can be a selection marker. Example includes, a gene resistant to herbicide such as glyphosate and phosphinothricin, and a gene resistant to antibiotics such as kanamycin, G418, bleomycin, hygromycin, and chloramphenicol, but not limited thereto.

According to the recombinant vector of the present invention, the promoter can be CaMV 35S promoter, actin promoter, ubiquitin promoter, pEMU promoter, MAS promoter, or histone promoter, but not limited thereto. The term "promoter" indicates a region of DNA located upstream of a structure gene, and it corresponds to a DNA molecule to which an RNA polymerase binds to initiate transcription. The term "plant promoter" indicates the promoter that can initiate transcription in a plant cell. The term "constitutive promoter" indicates the promoter that is active under most environmental conditions and cell growth or differentiation state. Since selection of a transformant can be made for various tissues at various stages, the constitutive promoter may be preferred for the present invention. Thus, selection property is not limited by a constitutive promoter.

In the above-described recombinant vector of the invention, any kind of a typical terminator can be used. Examples include, nopalin synthase (NOS), rice α-amylase RAmy1 A terminator, phaseolin terminator, and a terminator for Octopine gene of *Agrobacterium tumefaciens*, etc., but are not limited thereto. Regarding the necessity of terminator, it is generally known that such region can increase reliability and an efficiency of transcription in plant cells. Therefore, the use of terminator is highly preferable in view of the context of the present invention.

Any kind of a host cell known in the pertinent art can be used if stable and continuous cloning and expression of the vector of the present invention can be achieved in prokaryotic cells by using it. Examples include strains belonging to the genus *Bascillus* such as *E. coli* JM109, *E. coli* BL21, *E. coli* RR1, *E. coli* LE392, *E. coli* B, *E. coli* X 1776, *E. coli* W3110, *Bascillus subtilus, Bascillus thuringiensis*, and the like, *Salmonella typhimurium*, intestinal flora and strains such as *Serratia marcescens* and various *Pseudomonas* Spp. and the like.

In addition, when the vector of the present invention is transformed in a eukaryotic cell, a host cell such as *Saccharomyce cerevisiae*, an insect cell, a human cell (e.g., CHO cell line (Chinese hamster ovary), W138, BHK, COS-7, 293, HepG2, 3T3, RIN and MDCK cell line), a plant cell line and the like can be used. Preferably, the host cell is a plant cell.

When a host cell is a prokaryotic cell, transfer of the vector of the present invention into a host cell can be carried out according to $CaCl_2$ method, Hanahan's method (Hanahan, D., J. Mol. Biol., 166:557-580 (1983)), and an electroporation method, etc. In addition, when a host cell is a eukaryotic cell, the vector of the present invention can be transferred into a host cell according to a microscopic injection method, calcium phosphate precipitation method, an electroporation method, a liposome-mediated transformation, DEAE-dextran treatment method and a gene bombardment method, etc.

Plant transformation means any method by which DNA is delivered to a plant. Such transformation method does not necessarily have a period for regeneration and/or tissue culture. Transformation of plant species is now quite general not only for dicot plants but also for monocot plants. In principle, any transformation method can be used for introducing a hybrid DNA of the present invention to an appropriate progenitor cells. It can be appropriately selected from a calcium/polyethylene glycol method for protoplasts (Krens, F. A. et al., 1982, Nature 296, 72-74; Negrutiu I. et al., June 1987, Plant Mol. Biol. 8, 363-373), an electroporation method for protoplasts (Shillito R. D. et al., 1985 Bio/Technol. 3, 1099-1102), a microscopic injection method for plant components (Crossway A. et al., 1986, Mol. Gen. Genet. 202, 179-185), a particle bombardment method for various plants components (DNA or RNA-coated) (Klein T. M. et al., 1987, Nature 327, 70), or a (non-complete) viral infection method in *Agrobacterium tumefaciens* mediated gene transfer by plant invasion or transformation of fully ripened pollen or microspore (EP 0 301 316), etc. A method preferred in the present invention includes *Agrobacterium* mediated DNA transfer. In particular, so-called binary vector technique as disclosed in EP A 120 516 and U.S. Pat. No. 4,940,838 can be preferably adopted for the present invention.

Further, the present invention provides a method for producing a transgenic plant with increased cuticular wax biosynthesis, comprising transforming a plant cell with the recombinant vector containing MYB96 (myb domain protein 96) gene from *Arabidopsis thaliana*, and regenerating the transformed plant cell into a transgenic plant. Preferably, the MYB96 gene may consist of a nucleotide sequence of SEQ ID NO: 1. Preferably, the cuticular wax may have increased content of fatty acid, alcohol or alkane, but not limited thereto.

The method of the present invention comprises a step of transforming a plant cell with the recombinant vector of the present invention, and such transformation may be mediated by *Agrobacterium tumefaciens*. In addition, the method of the present invention comprises a step of regenerating a transformed plant cell to a transgenic plant. A method of regenerating a transformed plant cell to a transgenic plant can be any method that is well known in the pertinent art.

The transformed plant cell must be regenerated into whole plant. The technique for regeneration from callus or protoplast culture to a mature plant is well known in the art for a number of species.

Further, the present invention provides a transgenic plant and its seed with increased cuticular wax biosynthesis that is produced by the method. Preferably, the plant may be dicot plant, but not limited thereto.

The dicot plant may be Diapensiaceae, Clethraceae, Pyrolaceae, Ericaceae, Myrsinaceae, Primulaceae, Plumbaginaceae, Ebenaceae, Styracaceae, Symplocaceae, Symplocaceae, Oleaceae, Loganiaceae, Gentianaceae, Menyanthaceae, Apocynaceae, Asclepiadaceae, Rubiaceae, Polemoniaceae, Convolvulaceae, Boraginaceae, Verbenaceae, Labiatae, Solanaceae, Scrophulariaceae, Bignoniaceae, Acanthaceae, Pedaliaceae, Orobanchaceae, Gesneriaceae, Lentibulariaceae, Phrymaceae, Plantaginaceae, Caprifoliaceae, Adoxaceae, Valerianaceae, Dipsacaceae, Campanulaceae, Compositae, Myricaceae, Juglandaceae, Salicaceae, Betulaceae, Fagaceae, Ulmaceae, Moraceae, Urticaceae, Santalaceae, Loranthaceae, Polygonaceae, Phytolaccaceae, Nyctaginaceae, Aizoaceae, Portulacaceae, Caryophyllaceae, Chenopodiaceae, Amaranthaceae, Cactaceae, Magnoliaceae, Illiciaceae, Lauraceae, Cercidiphyllaceae, Ranunculaceae, Berberidaceae, Lardizabalaceae, Menispermaceae, Nymphaeaceae, Ceratophyllaceae, Cabombaceae, Saururaceae, Piperaceae, Chloranthaceae, Aristolochiaceae, Actinidiaceae, Theaceae, Guttiferae, Droseraceae, Papaveraceae, Capparidaceae, Cruciferae, Platanaceae, Hamamelidaceae, Crassulaceae, Saxifragaceae, Eucommiaceae, Pittosporaceae, Rosaceae, Leguminosae, Oxalidaceae, Geraniaceae, Tropaeolaceae, Zygophyllaceae, Linaceae, Euphorbiaceae, Callitrichaceae, Rutaceae, Simaroubaceae, Meliaceae, Polygalaceae, Anacardiaceae, Aceraceae, Sapindaceae, Hippocastanaceae, Sabiaceae, Balsaminaceae, Aquifoliaceae, Celastraceae, Staphyleaceae, Buxaceae, Empetraceae, Rhamnaceae, Vitaceae, Elaeocarpaceae, Tiliaceae, Malvaceae, Sterculiaceae, Thymelaeaceae, Elaeagnaceae, Flacourtiaceae, Violaceae, Passifloraceae, Tamaricaceae, Elatinaceae, Begoniaceae, Cucurbitaceae, Lythraceae, Punicaceae, Onagraceae, Haloragaceae, Alangiaceae, Cornaceae, Araliaceae or Umbelliferae (Apiaceae), but not limited thereto.

Further, the present invention provides a method for producing a biofuel using a cuticular wax, comprising separating and purifying a cuticular wax from the transgenic plant, and producing a biofuel from the separated and purified cuticular wax. A method for producing a biofuel from wax may use any method known in the art.

Preferably, the biofuel may be bioalcohol or biodiesel, but not limited thereto. Preferably, the bioalcohol may be bioethanol or biomethanol, but not limited thereto.

Further, the present invention provides a composition for increasing cuticular wax biosynthesis of plant, which comprises a MYB96 gene consisting of a nucleotide sequence of SEQ ID NO: 1 as effective component. The composition of the present invention comprises the MYB96 gene consisting of a nucleotide sequence of SEQ ID NO: 1 as effective component and cuticular wax biosynthesis of plant can be increased by transforming a plant with the MYB96 gene.

The present invention will now be described in greater detail with reference to the following examples. However, it is only to specifically exemplify the present invention and in no case the scope of the present invention is limited by these examples.

Methods

Plant Materials and Growth Conditions

All *Arabidopsis thaliana* lines used were in the Col-0 background. Plants were grown in a controlled culture room or on ½ X Murashige and Skoog (MS)-agar plates (hereafter referred to as MS-agar plates) at 22° C. under long day conditions (16-h light and 8-h dark). White light illumination (120 mmol photons $m^{-2}s^{-1}$) was provided by fluorescent FLR40D/A tubes (Osram, Seoul, Korea). The activation-tagged myb96-1D and T-DNA insertional myb96-1 mutants have been described previously (Seo et al., *Plant Physiol.* 151, 275-289, 2009).

The primers used for subcloning of the MYB96 gene under the control of a β-estradiol-inducible promoter were MYB96-F (5'-GGCTCGAGATGGGAAGACCACCTTGC, XhoI; SEQ ID NO: 2) and MYB96-R (5'-CCTTAATTAAC-TAGAACATCCCTTCTTGTCC, PacI; SEQ ID NO: 3). The PCR product was subcloned into the pER8 vector (Zuo et al., *Plant J.* 24, 265-273, 2000). Two-week-old plants grown on MS-agar plates were used to induce the MYB96 gene by 10 μM β-estradiol.

To examine the effects of growth hormones and stress conditions on gene expression, two-week-old plants grown on MS-agar plates were transferred to MS liquid cultures supplemented with 20 μM ABA or 100 μM SA and incubated for 6 h. To examine the effects of drought, plants were put on a dry 3MM paper and incubated at room temperature for 2 h. To examine the effects of high salinity, plants were soaked in MS liquid cultures containing 150 mM NaCl and incubated for 6 h. For cold treatments, plants were exposed to 4° C. for 24 h.

Microarray Assays

Two-week-old whole plants grown on MS-agar plates at 22° C. under long days were used for extracting total RNAs using the RNeasy Plant Mini Kit (Qiagen, Valencia, Calif.). The total RNA samples were pretreated with an RNase-free DNase I and cleaned up using the Plant Total RNA Isolation Kit (Qiagen). Three independent RNA samples were assayed and statistically treated. Probe preparation, hybridization to the GeneChip *Arabidopsis* ATH1 Genome Arrays (Affymetrix, Inc), and subsequent processing steps were carried out according to the manufacturer's procedure. Global normalization and expression estimates were analyzed by GC-robust multi-array (gcRMA) implemented in the bioconductor (http://www.bioconductor.org) and R software (Wu et al., *J. Am. Stat. Assoc.* 99, 909-917, 2004). False-discovery rates were calculated by significance analysis of microarrays algorithm (Gentleman, et al., *Genome Biol.* 5, R80, 2004), and genes with fold-change of at least 2 and a P-value lower than 0.05 were identified. The microarray dataset is deposited into ArrayExpress with accession number E-MEXP-2965 at http://www.ebi.ac.uk/at-miamexpress (under curation).

Analysis of Transcript Levels

Quantitative real-time RT-PCR (qRT-PCR) reactions were performed in 96-well blocks with an Applied Biosystems 7500 Real-Time PCR System using the SYBR Green I master mix in a volume of 25 μl. The reactions were carried out in biological triplicates using RNA samples extracted from three independent plant materials and gene-specific primers. Data processing and determination of the reaction specificities were carried out as described previously (Seo et al., *Plant Physiol.* 151, 275-289, 2009).

Scanning Electron Microscopy and Nile Red Staining

For cuticular wax crystal observation, the fourth rosette leaves or inflorescence stem segments from tip to 2 cm of 3-week-old plants grown in soil were examined by scanning electron microscopy (SEM) as described previously (Lee et al, *Plant J.* 60, 462-475, 2009).

For Nile red staining, plant materials were incubated for 20 min in a 5 ng $ml^{-1}$ Nile red solution. Stained samples were washed with deionized water and analyzed using a TCS SP5 AOBS/Tandem laser confocal scanning microscope (Leica, Wetzlar, Germany). Nile red was excited with 488 nm laser and collected with a 560-615 nm filter as described previously (Pighin et al, *Science* 306, 702-704, 2004).

Analysis of Cuticular Wax Composition and Loads

Cuticular waxes were extracted from the leaves (200 to 1000 mg) and stems (200 mg) of 4-week-old plants in chloroform for 30 s at room temperature. n-octacosane, docosanoic acid, and 1-tricosanol were added to the extracted chloroform solvent as internal standards. The solvent was subsequently evaporated under gentle stream of nitrogen and redissolved in a mixture of 100 μl of pyridine and 100 μl of bis-N,N-(trimethylsilyl)trifluoroacetamide. The wax mixtures were heated at 90° C. for 30 min to convert waxes into trimethylsilyl derivatives. Qualitative and quantitative composition analyses were conducted as described previously (Lee et al., *Plant J.* 60, 462-475, 2009).

Analysis of Cutin Polyester Monomers

Rosette leaves of 4-week-old plants grown in soil were used to quantify cutin polyester monomers. Methyl heptadecanoate and ω-pentadecalactone were added as internal standards into the delipidated and dried leaves and then depolymerized by hydrogenolysis with $LiAlH_4$ or by methanolysis with $NaOCH_3$. Cutin polyesters were analyzed by GC-MS (GCMS-QP2010; Shimazu, Kyoto, Japan) with a HP-5 column (60 m, 0.32 mm inner diameter, film thickness 0.1 mm; Agilent, Santa Clara, Calif.). The analysis system was maintained at 110° C. The temperature was increased to 300° C. at a rate of 2.5° C. $min^{-1}$ and maintained at 300° C. for 3 min.

Electrophoretic Mobility Shift Assays

The MYB96 gene was subcloned into the pMAL-c2X *E. coli* expression vector (NEB, Ipswich, Mass.) having a maltose binding protein (MBP)-coding sequence. The MBP-MYB96 fusion protein was purified according to the manufacturer's procedure using the pMAL™ Protein Fusion and Purification System (#E8000S). The DNA fragments were end-labeled with γ-32P [dATP] using T4 polynucleotide kinase. Labeled probes were incubated with approximately 0.5 μg of the purified MBP-MYB96 protein for 30 min at 25° C. in a binding buffer (10 mM Tris-HCl, pH 7.6, 50 mM NaCl, 1 mM EDTA, 5 mM DTT, 5% glycerol) with or without competitor DNA fragments. The reaction mixtures were electrophoresed on 6% native PAGE gels. The gels were dried on Whatman 3MM paper and exposed to X-ray films.

Chromatin Immunoprecipitation Assays

A MYC-coding sequence was fused in-frame to the 3' end of the MYB96 gene, and the gene fusion was subcloned under the Cauliflower Mosaic Virus (CaMV) 35S promoter. The expression construct was transformed into Col-0 plants. Two-week-old 35S:96-MYC transgenic plants grown on MS-agar plates were used for extraction of total protein extracts. The processing of plant materials and qRT-PCR were carried out as described previously (Lawrence et al., *Mol. Cell.* 13, 599-609, 2004).

Transcriptional Activation Activity Assays

The MYB96 gene sequence was fused in-frame to the 3' end of the GAL4 DNA-binding domain-coding sequence in the effector plasmid. The activity of the MYB96 transcription factor was examined by a GAL4 transient expression system using *Arabidopsis* protoplasts as described previously (Miura et al., *Plant Cell* 19, 1403-1414, 2007).

Chlorophyll Leaching Assays

Rosette leaves of 4-week-old plants grown in soil were used. The leaves were weighed, and approximately 2 g of each leaf sample was incubated on ice for 30 min and immersed in 30 ml of 80% ethanol in 50 ml conical tubes at room temperature. Aliquots of 100 μl were removed from the solution at every 10 min after initial immersion. The amount of extracted chlorophylls was quantified by measuring absorbance at 647 nm and 664 nm using a diode array spectrophotometer (WPA Biowave, Cambridge, UK) as described previously (Lolle et al., *Genetics* 149, 607-619, 1998).

Example 1

Expression of Cuticular Wax Biosynthetic Gene in myb96-1D and myb96-1 Mutants

Stomatal control of transpiration is a primary defense mechanism that prevents water loss under drought (Sirichandra et al., *J. Exp. Bot.* 60, 1439-1463, 2009). Yet, no evident changes in stomatal aperture occur in some drought-tolerant mutants (Cominelli et al., *Plant J.* 53, 53-64, 2008), showing that drought tolerance is not conferred only by stomatal closure. Recent studies support that cuticular wax deposition is closely associated with drought tolerance (Zhang et al., *Plant J.* 42, 689-707, 2005). However, little is known about how cuticular wax biosynthesis is regulated in response to drought.

The MYB96 transcription factor promotes drought tolerance: whereas the myb96-1D mutant is resistant to drought, the myb96-1 mutant is susceptible to drought (Seo et al., *Plant Physiol.* 151, 275-289, 2009). Accordingly, stomatal aperture is slightly altered in the mutants. However, we expected that additional traits would also contribute to drought tolerance. To obtain clues as to how MYB96 promotes drought tolerance, we carried out microarray assays using the Affymetrix GeneChip representing approximately 24,000 genes, and differentially expressed genes were identified after statistical analysis (>2-fold change; P<0.05).

Approximately 600 genes were up-regulated in the myb96-1D mutant (FIG. 1A). A major functional category of the up-regulated genes included those encoding a subset of wax biosynthetic enzymes (FIG. 1B), such as 3-ketoacyl-CoA synthase 1 (KCS1), KCS2, KCS6, 3-ketoacyl-CoA reductase 1 (KCR1), ECERIFERUM 1 (CER1), and CER3 (Beaudoin et al., *Plant Physiol.* 150, 1174-1191, 2009). Genes encoding putative wax transporters were also up-regulated in the mutant (FIG. 1C), suggesting that cuticular wax biosynthesis and transport are broadly influenced in the myb96-1D mutant. The microarray data were verified by quantitative real-time RT-PCR (qRT-PCR). Whereas the wax biosynthetic genes were up-regulated in the myb96-1D mutant, they were down-regulated in the myb96-1 mutant (FIG. 1D). Furthermore, the MYB96 gene was expressed to a high level in stem epidermal cells (data not shown), where cuticular waxes are synthesized (Suh et al., Plant Physiol. 139, 1649-1665, 2005), supporting that the MYB96 transcription factor is related to cuticular wax biosynthesis.

Example 2

Deposition Analysis of Cuticular Wax Crystal in myb96-1D and myb96-1 Mutants

We analyzed deposition of cuticular wax crystals on the leaf surface by scanning electron microcopy (SEM). Strikingly, cuticular wax crystals were drastically increased on the myb96-1D leaves ((a) of FIG. 2A). In contrast, they were significantly reduced on the myb96-1 stem. The glossy appearance largely disappeared on the myb96-1 stem ((b) of FIG. 2A). SEM and Nile red staining revealed that cuticular wax crystals were reduced accordingly on the mutant stem ((c) of FIG. 2A).

Measurements of cuticular wax contents and composition by gas chromatography-mass spectrometry (GC-MS) and GC showed that total wax load was elevated 8.6-fold in the myb96-1D leaves (FIG. 2B). Cuticular wax composition was also altered in the mutant leaves (FIG. 2B). Alterations in the contents of aldehydes and alkanes were the most prominent changes. In contrast, total wax load was decreased by approximately 34% in the myb96-1 leaves (FIG. 2C). It was also decreased to a similar degree in the myb96-1 stem (data not shown). However, deposition and composition of cutin monomers, which are the major components of cuticular lipids, and expression of cutin biosynthetic genes were not discernibly altered in the myb96-1D leaves (data not shown)

(Schnurr et al., *Plant Cell* 16, 629-642, 2004), indicating that MYB96 specifically regulates biosynthesis and accumulation of cuticular waxes.

Chlorophyll leaching assays, which are frequently used to examine cuticular defects on leaves (Chen et al., *Plant Cell* 15, 1170-1185, 2003), showed that chlorophyll bleaching occurred slowly in the myb96-1D leaves but quickly in the myb96-1 leaves (data not shown), which is certainly due to the differential accumulation of cuticular wax crystals. Collectively, these observations support the role of MYB96 in biosynthesis and accumulation of cuticular waxes.

Example 3

Expression Analysis of Cuticular Wax Biosynthetic Gene by Drought and ABA in myb96-1D and myb96-1 Mutants The MYB96 transcription factor induces drought resistance via an ABA signaling pathway (Seo et al., *Plant Physiol.* 151, 275-289, 2009). Therefore, we asked whether the selected wax biosynthetic genes are influenced by drought and ABA. All the genes examined, including KCS1, KCS2, KCS6, and KCR1, were significantly induced by exogenous application of ABA and exposure to drought (FIG. 3A). Furthermore, the effects of ABA on gene expression were greatly reduced in the myb96-1 mutant (FIG. 3B), showing that ABA induction of the genes is at least partially dependent on MYB96. Lipid biosynthetic genes, such as PLC1 and HSD1, were also induced by ABA. However, the ABA effects were independent of MYB96 (data not shown).

Example 4

Effect of MYB96 on Cuticular Wax Biosynthesis and Accumulation

We next examined whether drought induces cuticular wax biosynthesis. Consistent with the role of MYB96 in the ABA induction of wax biosynthetic genes, drought triggered accumulation of cuticular waxes (FIG. 4A). However, the positive effects of drought were significantly reduced in the myb96-1 leaves, which is in agreement with the notion that cuticular wax accumulation confers drought tolerance (Aharoni et al., Plant Cell 16, 2463-2480, 2004). Furthermore, composition of cuticular waxes was also significantly altered in the mutant leaves (FIG. 4B).

To examine more directly the role of MYB96 in cuticular wax biosynthesis, we produced transgenic *Arabidopsis* plants expressing the MYB96 gene under the control of a β-estradiol-inducible promoter and examined deposition of cuticular waxes on the leaves. Genes involved in wax biosynthesis, such as KCS1 and KCS2, were induced within 6 h after the inducer was added (FIG. 4C), confirming that MYB96 regulates the genes. Accordingly, deposition of cuticular wax crystals was increased on the transgenic leaves only after induction of the MYB96 gene (FIG. 4D). Together, these observations demonstrate that the induction of cuticular wax biosynthesis and accumulation by drought is mediated by MYB96.

Example 5

MYB96 Transcription Factor Specifically Binding to Promoter of Wax Biosynthetic Gene Transcriptional control of cuticular lipid biosynthesis has been recently documented (Raffaele et al., *Plant Cell* 20, 752-767, 2008). However, no specific transcription factors have been unequivocally proven to bind directly to the biosynthetic gene promoters. We therefore asked whether the MYB96 transcription factor regulates directly the cuticular wax biosynthetic genes identified from the microarray assays.

Sequence analysis revealed that promoters of the wax biosynthetic genes, such as KCS1, KCS2, KCS6, and KCR1, contain conserved sequence motifs (FIG. 5A), which are analogous to the MYB-binding consensus sequences (BS) (Abe et al., *Plant Cell* 15, 63-78, 2003). As inferred from sequence analysis, electrophoretic mobility shift assays (EMSA) using a recombinant MBP (maltose-binding protein)-MYB96 fusion protein produced in *E. coli* cells showed that the MYB96 protein bound specifically to the BS sequence motifs (FIG. 5B). Whereas the MYB96 binding was significantly reduced in the presence of excess amounts of unlabelled BS fragments, it was reduced to a lesser degree by mutated DNA fragments (mBS), supporting the specific binding of MYB96 to the BS sequences. Notably, the MYB96 protein bound to the BS sequences present only in the promoters of the genes encoding rate-limiting enzymes involved in cuticular wax biosynthesis (data not shown), such as KCS1, KCS2, KCS6, and KCR (Beaudoin et al., *Plant Physiol.* 150, 1174-1191, 2009).

Chromatin immunoprecipitation (ChIP) assays were employed to confirm the binding of MYB96 to the gene promoters using the 35S:96-MYC transgenic plants, in which a MYC-coding sequence was fused in-frame to the 3' end of the MYB96 gene, and an anti-MYC antibody. Quantitative real-time ChIP-PCR assays showed that the MYB96 protein binds to the gene promoters in planta in identical patterns to those observed in the EMSA assays (FIG. 5C).

We next carried out transient 3-glucuronidase (GUS) expression assays in *Arabidopsis* protoplasts to further investigate the MYB96 regulation of wax biosynthetic genes. The KCS1-BS and -mBS DNA fragments were transcriptionally fused to a Cauliflower Mosaic Virus (CaMV) 35S minimal promoter in the pCAMBIA1305.1 plasmid containing the GUS reporter gene, resulting in pKCS-P or pKCS-mP (FIG. 5D). The reporter plasmids and an effector plasmid p35S-MYB96 were cotransformed into *Arabidopsis* protoplasts. A vector construct containing the luciferase gene was included to monitor transformation efficiencies (Miura et al., *Plant Cell* 19, 1403-1414, 2007). The cotransformation of p35S-MYB96 with pKCS-P was found to elevate the reporter gene expression more than 6-fold (FIG. 5E). In contrast, cotransformation with pKCS-mP did not elevate the reporter gene expression, indicating that MYB96 acts as a transcriptional activator of wax biosynthetic genes.

Altogether, our data demonstrate that the MYB96 transcription factor regulates directly the genes encoding rate-limiting enzymes involved in cuticular wax biosynthesis under drought, thus rendering tolerance to drought (FIG. 5F) (Kunst and Samuels, *Curr. Opin. Plant Biol.* 12, 721-727, 2009). This signalling pathway is distinct from the ABA signalling pathways governing stomatal regulation (Cominelli et al., *Plant J.* 53, 53-64, 2008), although it is still possible that the MYB96 transcription factor contributes at least in part to stomatal regulation via the RD22 gene (Seo et al., *Plant Physiol.* 151, 275-289, 2009). Our data also indicate that *Arabidopsis* is a potential model system for studies on cuticular wax biosynthesis under drought. It is particularly noteworthy that endogenous content of alkanes, a major constituent of gasoline and diesel, was increased more than 8-fold in the myb96-1D mutant, suggesting that our finding would be applicable to engineering of alkane biosynthesis in higher plants (Schirmer et al., *Science* 329, 559-562, 2010).

What is claimed is:

1. A method for obtaining cuticular wax, the method comprising:
    transforming a plant cell with a recombinant vector containing an MYB96 (myb domain protein 96) gene from *Arabidopsis thaliana*;
    regenerating the transformed plant cell into a transgenic plant; and
    separating cuticular wax from the transgenic plant to obtain the cuticular wax.

2. The method according to claim 1, wherein the MYB96 gene consists of the nucleotide sequence of SEQ ID NO: 1.

3. The method according to claim 1, wherein the cuticular wax comprises fatty acid, alcohol or alkane.

4. A method for producing a biofuel, comprising:
    transforming a plant cell with a recombinant vector containing an MYB96 (myb domain protein 96) gene from *Arabidopsis thaliana*;
    regenerating the transformed plant cell into a transgenic plant;
    separating and purifying a cuticular wax from the transgenic plant; and
    producing a biofuel from the separated and purified cuticular wax.

5. The method according to claim 4, wherein the biofuel is bioalcohol or biodiesel.

6. The method according to claim 5, wherein the biofuel is bioethanol or biomethanol.

* * * * *

SEQUENCE LISTING

<160> NUMBER OF SEQ ID NOS: 5

<210> SEQ ID NO 1
<211> LENGTH: 1059
<212> TYPE: DNA
<213> ORGANISM: Arabidopsis thaliana

<400> SEQUENCE: 1

| | | | | | | |
|---|---|---|---|---|---|---|
| atgggaagac | caccttgctg | tgaaaagatt | ggagtgaaga | aagggccatg | gacaccagag | 60 |
| gaagacatca | tcttggtttc | ttacatccaa | gaacatggtc | ctggaaactg | gagatctgtc | 120 |
| ccaacacaca | caggtttgag | aagatgtagc | aagagctgca | gattgagatg | gactaattat | 180 |
| cttcgacccg | gtattaagcg | tggaaatttt | actgagcatg | aagagaagac | aattgttcat | 240 |
| cttcaagccc | ttttaggcaa | cagatgggca | gccatagcat | cataccttcc | agaaaggaca | 300 |
| gacaatgata | taaagaacta | ttggaacact | cacttgaaga | agaagctcaa | aaagattaat | 360 |
| gaatctggtg | aagaagataa | tgatggtgtc | tcttcatcaa | acactagttc | acaaaagaac | 420 |
| catcaaagca | ctaacaaagg | tcaatgggaa | agaagacttc | agacagacat | taacatggca | 480 |
| aaacaagctc | tttgtgaggc | cttgtcttta | gacaaaccat | catccactct | ttcatcatct | 540 |
| tcatcattac | cgacaccagt | aatcacacaa | caaaacatcc | gtaacttctc | atcagctttg | 600 |
| cttgaccgtt | gttatgatcc | atcctcttct | tcttcatcta | ccacaaccac | cactacaagc | 660 |
| aacactacta | atccataccc | atcaggggta | tatgcgtcaa | gtgctgagaa | catcgcccgg | 720 |
| ttgcttcaag | atttcatgaa | agacacaccc | aaggctttaa | ctttatcatc | ttcatctccg | 780 |
| gtttcagaga | ctggaccact | cactgctgca | gtctcggaag | aaggtggaga | agggtttgaa | 840 |
| caatctttct | tcagcttcaa | ttcaatggac | gaaactcaaa | acttgactca | ggagacaagc | 900 |
| ttcttccatg | atcaagtgat | caaaccggaa | ataacaatgg | accaagatca | tggtctaata | 960 |
| tcacaagggt | ctctgtcttt | gtttgagaaa | tggttatttg | atgagcaaag | ccacgagatg | 1020 |
| gttggtatgg | cactagcagg | acaagaaggg | atgttctag | | | 1059 |

<210> SEQ ID NO 2
<211> LENGTH: 26
<212> TYPE: DNA
<213> ORGANISM: Artificial Sequence
<220> FEATURE:
<223> OTHER INFORMATION: MYB96-F primer

<400> SEQUENCE: 2
ggctcgagat gggaagacca ccttgc                                     26

<210> SEQ ID NO 3
<211> LENGTH: 31
<212> TYPE: DNA
<213> ORGANISM: Artificial Sequence
<220> FEATURE:
<223> OTHER INFORMATION: MYB96-R primer

<400> SEQUENCE: 3
ccttaattaa ctagaacatc ccttcttgtc c                               31

<210> SEQ ID NO 4
<211> LENGTH: 97
<212> TYPE: DNA
<213> ORGANISM: Arabidopsis thaliana

<400> SEQUENCE: 4

-continued

```
aataactaga aaaatactcg aaaactaact agagtcccta actactaact atattcaaga    60
ttaactgtat tcagttgcag ttaagataac tgcagat                             97

<210> SEQ ID NO 5
<211> LENGTH: 97
<212> TYPE: DNA
<213> ORGANISM: Arabidopsis thaliana

<400> SEQUENCE: 5
aaggggggga aaaatactcg aaaacggggg ggagtcccgg ggggcggggg gtattcaaga    60 tgggggtat tcagttgggg gggagagggg ggcagat                              97
```